United States Patent [19]

Traynor et al.

[11] 4,209,554

[45] Jun. 24, 1980

[54] POLYDENTATE METAL SALTS USED IN THE PROCESS FOR THE DEACTIVATION OF GLASS SURFACES AND CAPILLARY COLUMNS THEREWITH

[75] Inventors: Sean G. Traynor; George Marcelin, both of Jacksonville, Fla.

[73] Assignee: SCM Corporation, New York, N.Y.

[21] Appl. No.: 14,131

[22] Filed: Feb. 22, 1979

[51] Int. Cl.$^2$ .................... B01D 53/04; B01D 15/08
[52] U.S. Cl. ........................................ 427/230; 55/67;
210/31 C
[58] Field of Search .................. 55/67; 210/31 C; 260/606.5 P, 440, 446; 427/230

[56] References Cited

U.S. PATENT DOCUMENTS

| | | | |
|---|---|---|---|
| 3,488,922 | 1/1970 | Kirkland | 55/67 |
| 3,722,181 | 3/1973 | Kirkland | 55/67 |
| 4,054,432 | 10/1977 | Taylor | 427/230 |

*Primary Examiner*—Sam Silverberg
*Attorney, Agent, or Firm*—A. Joseph Gibbons

[57] ABSTRACT

Phosphonium salts are prepared by reacting polydentate phosphines containing two or more trivalent phosphorus atoms with alkyl or aralkyl halides. Treatment of glass surfaces and glass capillary columns with these salts substantially eliminates tailing of peaks and allow the high temperature separation and characterization of polar compounds by gas chromatography at temperatures of 300° C.

8 Claims, 1 Drawing Figure

POLYDENTATE METAL SALTS USED IN THE PROCESS FOR THE DEACTIVATION OF GLASS SURFACES AND CAPILLARY COLUMNS THEREWITH

BACKGROUND OF THE INVENTION

This invention relates to new polydentate salts prepared from polydentate phosphines containing at least two and preferably at least four trivalent phosphorus atoms or their antimony or arsenic analogs and their use in deactivating glass capillary columns for high temperature analysis of polar compounds via gas chromatographic techniques.

Gas chromatography techniques using glass capillary columns in conjunction with flame ionization detectors have developed as an analytical tool over the past two decades. Complex mixtures of hydrocarbons can be separated into their component parts using open tubular columns. The use of glass as a base material for capillary columns is advantageous because of its low catalytic activity and relative inertness to labile substances in complex mixtures. Such columns suffer from the disadvantage that components of polar mixtures are more strongly attached to the column wall. Thus, when the operating temperature is increased above 150° C. the carrier gas tends to dislodge the column liquid phase from the glass surface causing decreased resolution by peak tailing.

This problem has been partly resolved by adding surface active material to the liquid coating phase to eliminate the effect of column wall. Various surfactants thus increased the useful operating temperature to about 170° C. Other techniques (Metcalf, L.D. and Martin, R. J., *Anal. Chem.* 1204 [1967]) using trioctadecylmethylammonium bromide as an additive extended the useful temperature range of capillary columns to about 200° C. By combining benzyltriphenylphosphonium chloride with various high temperature phases, Malec [J. Chromatog. Sci., 9, 319 (1971)] was successful in overcoming resolution difficulties and produced columns useful at about 250° C. In the gas chromatographic analysis of polar mixtures, there is a need to provide capillary columns that will withstand even higher temperatures whereby substrate bleeding and peak tailing is eliminated using columns operated routinely at 300° C. and above.

BRIEF SUMMARY OF THE INVENTION

A primary object of this invention is to prepare novel phosphonium salts by the quaternization of polydentate phosphines containing two or more trivalent phosphorus atoms.

Another object relates to a process for treating glass capillary surfaces with one or more of the herein described phosphonium salts or their antimony or arsenic analogs.

A further object relates to a process for deactivating capillary columns and the use of such deactivated columns in the gas chromatographic analysis of complex mixtures including polar compounds at operating temperatures of 300° C. and above.

A further object relates to a process for preparing a glass capillary column capable of resolving complex mixtures of polar compounds at useful temperatures of 300° C. and above:

(a) by etching the glass surface with a hydrogen halide;

(b) contacting the etched surface with a solution of one or more polydentate phosphonium salts containing two or more and preferably at least four trivalent phosphorus atoms to deactivate the glass surface;

(c) treating the deactivated columns with one or more liquid phases capable of resolving said complex polar compounds;

(d) thereafter drying the column and conditioning the dried column at a temperature of about 300° C. and above.

Other and further objects, features and advantages of this invention will appear more fully from the following description.

DETAILED DESCRIPTION OF THE INVENTION

Figure 1:
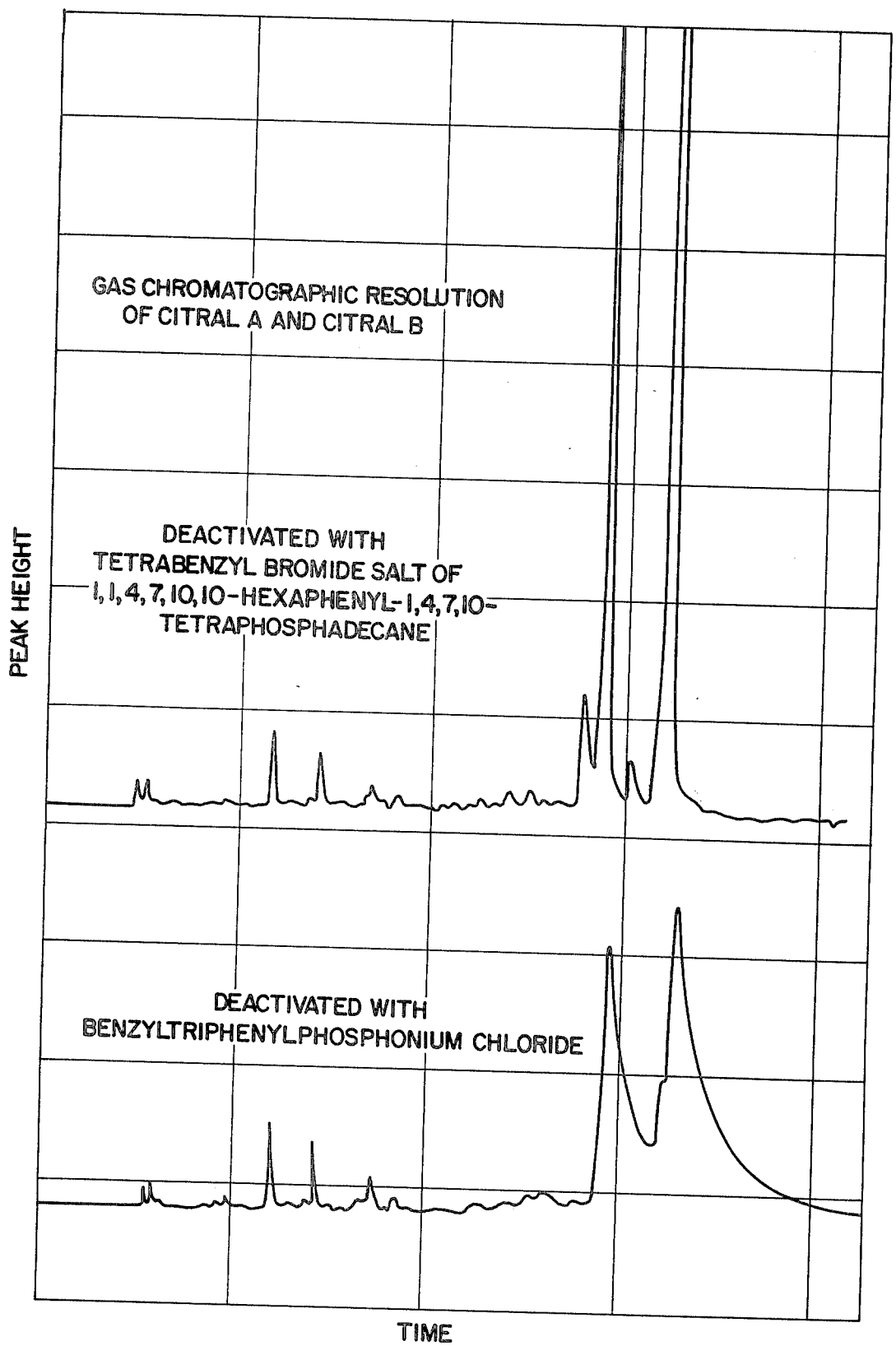

The polydentate phosphonium salts of the instant invention can be prepared by usual quaternization techniques. The polydentate can be dissolved in a solvent and one equivalent (per each trivalent phosphonium atom) of alkyl halide or aralkyl halide in a solvent added slowly thereto with stirring under a reflux condenser and an inert atmosphere followed by stirring and reflux as needed to complete the reaction. Alternatively, excess halide can be used as the reaction medium, in which case the polydentate is added directly thereto. The reaction products are usually crystalline solids which may be isolated by filtration and purified by recrystallization.

Polydentate compounds useful in the practice of this invention include those obtained by partial or complete quaternization of polydentate phosphines containing two or more trivalent phosphorus atoms or their antimony or arsenic analogs. The following structures are representative of such polydentate compounds:

(1) $R_1R_2MAMR_1R_2$;
(2) $(R_1R_2MA)_3P$;
(3) $(R_1R_2MA)_2MR_3$;
(4) $(R_1R_2MA)_2MAM(AMR_1R_2)_2$; and

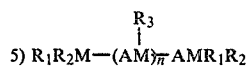

5) $R_1R_2M-(AM)_{\overline{n}}AMR_1R_2$ wherein M is independently a group V-A element selected from the group consisting of phosphorus, antimony and arsenic; $R_1$, $R_2$ and $R_3$ are the same or different $C_{1-20}$ alkyl radicals or aromatic radicals containing up to twelve carbon atoms; and A represents a lower alkylene radical containing from 2 to 6 carbons, and n is an integer from 1 to 6. Useful quaternary salt forming compounds include mono or difunctional alkyl or aralkyl halide selected from the group consisting of (1) $R_4X$; (2) $ArR_5X$; (3) $XR_6X$; and (4) $XCH_2ArCH_2X$ wherein X is halogen; $R_4$ is an alkyl radical containing up to 20 carbon atoms; $R_5$ is a lower alkylene radical containing 1 to 4 carbon atoms; and $R_6$ is a lower alkylene radical containing 2 to 6 carbon atoms; Ar is a monovalent or divalent aryl radical which may contain one or more halogen ring substituents and when Ar is a divalent radical, the compound may contain one or more aryl groups.

In the instant invention, phosphonium salts are preferred because of the stability and availability of the polytertiary phosphines. Useful polydentates include those exemplified in U.S. Pat. No. 3,130,237 (Wald) and the phosphines, arsines and arsinophosphines described by King and Kapoor in U.S. Pat. No. 3,657,298.

Flint glass capillary columns were drawn using a Schimadzu GDM-1 capillary drawing machine and then etched with a hydrogen halide at a temperature in the range of 300°–450° C. for 1 to 4 hours. After cooling to ambient temperature, a solution of the phosphonium halide dissolved in a solvent is then percolated through the column under positive nitrogen atmosphere. Nitrogen flow is continued and the column allowed to dry. The column is then treated with the appropriate liquid substrate in a solvent, dried under nitrogen and conditioned by further heating until a stable base line is obtained. The above treatment will result in uniformly treated columns which may be operated routinely at 300° C. and above, at high column efficiency with no substantial peak tailing.

The alkyl and aralkyl halides useful in preparing the phosphonium salts of this invention include the fluorides, chlorides, bromides and iodides of $C_{1-20}$ alkyl halides and aralkyl halides. The aryl moiety may have one or more substituents in the aromatic ring portion selected from the group consisting of lower alkyl and halogen, provided they do not interfere with the quaternization reaction. Preferred mono functional halides include methyl, ethyl, and benzylbromides, chlorides, fluorides and iodides with the bromides being especially advantageous because of their availability and reactivity.

Also contemplated as reactive halides in the quaternization reaction are double ended halides of the formula X—R—X. Preferred multifunctional halides include 1,2-dibromoethane; 1,3-dibromopropane; 1,4-dibromobutane; and α,α'-dibromo-p-xylene with the latter two compounds being especially preferred. Phosphonium compounds selected from multifunctional halides will generally be highly cross-linked and thus having a higher decomposition temperature. They are generally soluble in polar solvents from which they may be purified by recrystallization techniques.

The following examples are intended to illustrate the invention, but not to limit the scope thereof, parts and percentages being by weight unless otherwise indicated.

EXAMPLE 1

Tetrabenzylbromide Salt of 1,1,4,7,10,10-hexaphenyl-1,4,7,10-tetraphosphadecane

An excess of benzylbromide, 36 g., was charged to a 50 ml round bottom flask having a stirring bar and fitted with a reflux condenser. 0.5 grams 1,1,4,7,10,10-hexaphenyl-1,4,7,10-tetraphosphadecane was added and the mixture refluxed under nitrogen for 2 hours. The product was isolated as a light brown precipitate by filtration under a nitrogen blanket.

Calculated for $C_{70}H_{70}P_4Br_4$: C,62.05; H,5.21; P,9.15; Br,23.59. Found: C,59.58; H,5.58; P,9.24; Br,25.61.

EXAMPLE 2

Tetrabenzylbromide Salt of Tris(2-diphenylphosphinoethyl)phosphine

In a procedure similar to that given in Example 1, tris(2diphenylphosphinoethyl)phosphine was reacted with excess benzyl bromide. The product was isolated as a brown solid by filtration under a nitrogen blanket.

Calculated for $C_{70}H_{70}P_4Br_4$: C,62.05; H,5.21; P,9.15; Br,23.59. Found: C,62.53; H,5.07; P,9.04; Br,23.35.

EXAMPLE 3

Preparation of Tribenzylbromide Salt of 1,1,4,7,7-pentaphenyl-1,4,7-triphosphaheptane Using a procedure similar to that given in Example 1, 1,1,4,7,7-pentaphenyl-1,4,7-triphosphaheptane was reacted with an excess of benzyl bromide. The product was isolated as a white solid.

EXAMPLE 4

Preparation of Di(benzyl bromide)Salt of 1,1,4,4-tetraphenyl 1,4-diphosphabutane Using a procedure similar to that given in Example 1, 1,1,4,4-tetraphenyl 1,4-diphosphabutane was reacted with an excess of benzyl bromide. The product, a known compound, was isolated as a white solid.

EXAMPLE 5

A flint glass capillary column approximately 60 meters in length and 0.25 mm in internal diameter was fabricated using a Shimadzu GDM-1 glass drawing machine. The column was etched with hydrogen chloride gas at 350° C. for 2 hours according to the method described by Franken et al., *J. Chromatog;* 126, 117–132 (1976). After cooling 3 ml of a 1 percent solution of the phosphonium salt of Example 1 dissolved in dimethylsulfoxide was passed through the column immediately followed by 2 ml of a 15 percent solution of SP-2100 (Supelco Inc.) dissolved in methylene chloride using the mercury plug technique as described by G. Schombey et al, *Chromatographia* 8, 486 (1975).

A second column using SP-2100 substrate but deactivated with benzyltriphenylphosphonium chloride was prepared under identical conditions. The column deactivated with the salt 1,1,4,7,10,10-hexaphenyl-1,4,7,10-tetraphosphadecane was usable at operating temperatures programmable to 300° C. and above whereas the column deactivated with benzyltriphenylphosphonium chloride rapidly deteriorated at this temperature.

EXAMPLE 6

Two 20 m glass capillary columns were prepared according to the procedure of Example 5 using 1,1,4,7,10,10-hexaphenyl-1,4,7,10-tetraphosphadecane and benzyltriphenylphosphonium chloride deactivators respectively. Each column was evaluated using a Hewlett-Packard Model No. 5750 gas chromatograph having a flame ionization detector. The columns were conditioned at 275° C. for 16 hours under a helium gas flow. After cooling to 150° C., a hexane solution containing 1-hexanol, n-decane, 5-nonanone and 2,5-dimethylaniline was analyzed in each column and the respective tailing factors for each component were compared as shown in the following table. It is noted that high tailing factors indicate good resolution, whereas low tailing factors indicate poor resolution and undesirable peak tailing.

| | Tailing Factor (Average of 2 Evaluations) | |
|---|---|---|
| | Benzyltriphenylphosphonium Chloride | Compound of Example 1 |
| 1-hexanol | 12.9 | 66.2 |
| n-decane | 95.6 | 96.9 |
| 5-nonanone | 27.5 | 88.6 |
| 2,5-dimethylaniline | 67.1 | 88.3 |

As indicated, the column deactivated with the compound of Example 1 exhibited greatly improved peak symmetry (reduced tailing) over the column deactivated with benzyltribenzylphosphonium chloride.

EXAMPLE 7

The comparative experiment as described in Example 6 was repeated using a more complex mixture containing the cis trans isomers Citral A (neral) and Citral B (geranial). The column deactivated with the compound of Example 1 gave markedly improved resolution and substantially no peak tailing as contrasted to the column deactivated with benzyltriphenylphosphonium chloride. The respective graphs of peak heights v. time are shown in FIG. 1. The major peaks represent Citral A (left) and Citral B (right).

EXAMPLE 8

Comparative Evaluation of Column Deactivants

The temperature dependence of various deactivation treatments was determined by connecting a treated but uncoated (no substrate) column and raising the temperature to the desired test temperature. After heating for a period of 3 hours, the temperature was lowered to 150° C. and a series of six compounds-each representing a different chemical functionality-was evaluated. The degree of deactivation was expressed as the tailing factor as described by Schiehe and Pretorius, *J. Chromatog.* 132, 217 (1977). The test compounds were (a) n-decane; (b) n-hexanol; (c) 2-nonanone; (d) 2,5-dimethylaniline; (d) salicylaldehyde; and (f) linalyl acetate. The average tailing factor for each of the deactivator compounds are given below:

| Deactivator | Average Tailing Factor | | |
|---|---|---|---|
|  | (250° C.) | (275° C.) | (300° C.) |
| Benzyltriphenylphosphonium Chloride | 68 | 19 | — |
| Toasted Carbowax 20 M | 36 | 14 | — |
| Example 1 - Phosphonium Salt | 64 | 64 | 47 |
| Example 2 - Phosphonium Salt | 70 | 66 | 62 |
| Example 3 - Phosphonium Salt | 40 | 38 | — |
| Example 4 - Phosphonium Salt | 32 | 26 | — |

What is claimed is:

1. A process for deactivating glass capillary columns which comprises treating the internal surfaces of a capillary column with one or more deactivating polydentate salts either prior to or in conjunction with the application of liquid substrate capable of separating complex mixtures of compounds using gas chromatographic techniques wherein the said columns are operated up to 300° C. and above and wherein the salts comprise the reaction product of
    (a) a polydentate compound containing two or more quaternizable group V-A elements of the following formula:
    (1) $R_1R_2MAMR_1R_2$;
    (2) $(R_1R_2MA)_3M$;
    (3) $(R_1R_2MA)_2MR_3$;
    (4) $(R_1R_2MA)_2MAM(AMR_1R_2)_2$; and (5) $R_1R_2M-(AM)_{\overline{n}}AMR_1R_2$
    $\quad\quad\quad\quad\quad\quad |$
    $\quad\quad\quad\quad\quad\quad R_3$ wherein M is independently a group V-A element selected from the group consisting of phosphorus, antimony and arsenic; $R_1$, $R_2$ and $R_3$ are the same or different $C_{1-20}$ alkyl radical, or an aromatic radical containing up to twelve carbon atoms and A represents a straight chain or branched lower alkylene radical containing from 2 to 6 carbons; n is an integer from 1 to 6; and
    (b) a quaternary salt forming mono or difunctional alkyl or aralkyl halide selected from the group consisting of (1) $R_4X$; (2) $ArR_5X$; (3) $XR_6X$; and (4) $XCH_2MCH_2X$ wherein X is halogen; $R_4$ is an alkyl radical containing 2 to 6 carbon atoms; $R_6$ is lower alkylene radical containing 2 to 6 carbon atoms; Ar is a mono or divalent aryl radical which may contain one or more halogen ring substituents.

2. The process of claim 1 wherein the polydentate salt is prepared from a phosphine selected from the group consisting of
    (a) 1,1,4,4-tetraphenyl 1,4-diphosphabutane;
    (b) tris(2-diphenylphosphinoethyl)phosphine;
    (c) 1,1,4,7,7-pentaphenyl-1,4,7-triphosphaheptane;
    (d) 1,1,4,7,10,10-hexaphenyl-1,4,7,10-tetraphosphadecane.

3. The process of claim 1 wherein the said phosphines are substantially completely quaternized with benzylbromide.

4. The process of claim 1 wherein the said phosphine is quaternized with 1,4-dibromobutane.

5. The process of claim 1 wherein the said phosphine is quaternized with α,α'-dibromo-p-xylene.

6. The process of claim 3 wherein the phosphine is 1,1,4,7,7-pentaphenyl-1,4,7-triphosphaheptane.

7. The process of claim 3 wherein the phosphine is 1,1,4,7,10,10-hexaphenyl-1,4,7,10-tetraphosphadecane.

8. A process for preparing glass capillary columns useful in analyzing complex mixtures of compounds by gas chromatographic techniques at operating temperatures up to 300° C. and above which comprises
    (a) pretreating the internal surfaces of a capillary column with one or more hydrogen halides at column temperatures in the range of 300° C. to 450° C. for 1 to 4 hours;
    (b) cooling the treated column under a nitrogen purge to room temperature;
    (c) under a positive inert gas pressure treating the column with a solution of one or more surface deactivating polydentate salts prepared from polydentate phosphines containing two or more trivalent phosphorus atoms or their antimony or arsenic analogs;
    (d) drying the column under an inert atmosphere;
    (e) coating the cooled column with a liquid substrate useful in separating complex mixtures of organic compounds; and
    (f) conditioning the coated column at temperatures up to the maximum operating temperature of the chromatographic substrate.

* * * * *